(12) United States Patent
Hayakawa et al.

(10) Patent No.: US 10,046,506 B2
(45) Date of Patent: Aug. 14, 2018

(54) BLOW MOLDING MACHINE AND METHOD FOR STERILIZING THE SAME

(71) Applicant: Dai Nippon Printing Co., Ltd., Tokyo (JP)

(72) Inventors: Atsushi Hayakawa, Tokyo (JP); Yoshinori Sato, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 0 days.

(21) Appl. No.: 15/109,867

(22) PCT Filed: Feb. 18, 2015

(86) PCT No.: PCT/JP2015/054388
§ 371 (c)(1),
(2) Date: Jul. 6, 2016

(87) PCT Pub. No.: WO2015/125808
PCT Pub. Date: Aug. 27, 2015

(65) Prior Publication Data
US 2016/0325482 A1   Nov. 10, 2016

(30) Foreign Application Priority Data

Feb. 19, 2014 (JP) ................. 2014-029369
Dec. 25, 2014 (JP) ................. 2014-262116

(51) Int. Cl.
*A61L 2/18* (2006.01)
*B29C 49/46* (2006.01)
(Continued)

(52) U.S. Cl.
CPC ............... *B29C 49/46* (2013.01); *A61L 2/18* (2013.01); *A61L 2/186* (2013.01); *A61L 2/22* (2013.01);
(Continued)

(58) Field of Classification Search
CPC ....... B29C 49/46; A61L 2/186; A61L 2202/15
See application file for complete search history.

(56) References Cited

U.S. PATENT DOCUMENTS

| 8,435,024 B2 | 5/2013 | Dordoni |
| 2003/0165400 A1* | 9/2003 | Hayakawa ............... A61L 2/04 422/28 |

(Continued)

FOREIGN PATENT DOCUMENTS

| DE | 10 2007 050 582 A1 | 4/2009 |
| DE | 10 2008 038 143 A1 | 2/2010 |

(Continued)

OTHER PUBLICATIONS

International Search Report and Written Opinion (Application No. PCT/JP2015/054388) dated Apr. 21, 2015.
(Continued)

*Primary Examiner* — Kevin Joyner
(74) *Attorney, Agent, or Firm* — Burr & Brown, PLLC (57) ABSTRACT

A blow molding machine is simply sterilized.
The blow molding machine is sterilized by filling a preform (1) with a liquid sterilizer (P) containing an ethanol constituent or both an ethanol constituent and a hydrogen peroxide constituent, and blasting blow air into the preform (1) in a state where the liquid sterilizer (P) remains in the preform (1) to diffuse the liquid sterilizer (P).

5 Claims, 8 Drawing Sheets (51) Int. Cl.
    *B65B 55/10* (2006.01)
    *A61L 2/22* (2006.01)
    *B29C 49/06* (2006.01)
    *B29C 49/36* (2006.01)
    *B29C 49/64* (2006.01)
    *B29K 67/00* (2006.01)
    *B29L 31/00* (2006.01)

(52) U.S. Cl.
    CPC ........... *B65B 55/10* (2013.01); *A61L 2202/15* (2013.01); *A61L 2202/23* (2013.01); *B29C 49/06* (2013.01); *B29C 49/36* (2013.01); *B29C 49/6418* (2013.01); *B29C 2049/4697* (2013.01); *B29K 2067/003* (2013.01); *B29L 2031/7158* (2013.01)

(56) References Cited

U.S. PATENT DOCUMENTS

| | | |
|---|---|---|
| 2007/0084771 A1 | 4/2007 | Watanabe et al. |
| 2008/0152538 A1* | 6/2008 | Quetel ................ A61L 2/04 422/28 |
| 2010/0303946 A1 | 12/2010 | Voth |
| 2011/0037187 A1 | 2/2011 | Winzinger et al. |
| 2011/0037188 A1 | 2/2011 | Hirdina |
| 2011/0133370 A1 | 6/2011 | Engelhard et al. |
| 2011/0248429 A1 | 10/2011 | Maeda et al. |
| 2011/0285063 A1 | 11/2011 | Chauvin et al. |
| 2011/0311675 A1 | 12/2011 | Voth et al. |
| 2012/0288406 A1 | 11/2012 | Iwashita et al. |
| 2013/0118534 A1 | 5/2013 | Winzinger et al. |
| 2013/0280127 A1 | 10/2013 | Voth |
| 2014/0054812 A1 | 2/2014 | Hirdina |
| 2014/0178519 A1 | 6/2014 | Winzinger et al. |

FOREIGN PATENT DOCUMENTS

| | | |
|---|---|---|
| EP | 2 283 991 A2 | 2/2011 |
| EP | 2 394 950 A1 | 12/2011 |
| JP | 2000-326935 A1 | 11/2000 |
| JP | 2009-274309 A1 | 11/2009 |
| JP | 2010-235209 A1 | 10/2010 |
| JP | 2010-274651 A1 | 12/2010 |
| JP | 2011-042169 A1 | 3/2011 |
| JP | 2011-046189 A1 | 3/2011 |
| JP | 2011-051337 A1 | 3/2011 |
| JP | 2011-147673 A1 | 8/2011 |
| JP | 2011-527246 A1 | 10/2011 |
| JP | 2012-500135 A1 | 1/2012 |
| JP | 2013-504456 A | 2/2013 |
| WO | 2005/047190 A1 | 5/2005 |
| WO | 2010/070846 A1 | 6/2010 |
| WO | 2012/092921 A1 | 7/2012 |
| WO | 2013/099789 A1 | 7/2013 |

OTHER PUBLICATIONS

Notice of Final Rejection, Japanese Application No. 2014-262116, dated May 17, 2016 (3 pages).
Partial Supplementary European Search Report (Application No. 15752147.7) dated Sep. 14, 2017.
Extended European Search Report (Application No. 15752147.7) dated Jan. 19, 2018.

* cited by examiner

FIG.1

FIG.2(A) SUPPLY STERILIZER

FIG.2(B) HEAT

FIG.2(C) MOLD

BLOW MOLDING MACHINE AND METHOD FOR STERILIZING THE SAME

TECHNICAL FIELD

The present invention relates to a blow molding machine and a method for sterilizing the same.

BACKGROUND ART

According to prior art, it is proposed to sterilize a preform before a blow molding machine molds the preform into a bottle or other container in a molding die (see Patent Document 1, for example). An aseptic package can be produced by filling such a bottle with an aseptic content and sealing the bottle.

However, during operation of the blow molding machine, various failures can occur in the blow molding machine. In such a case, it is necessary to stop the blow molding machine, open a cover of a chamber or the like over the blow molding machine, and open the molding die or the like to inspect the interior thereof. When the blow molding machine is opened and disassembled or maintained, microorganisms from the environment including an operator can enter the blow molding machine and adhere to the molding die, an extension rod or the like and to the preform or the bottle, thereby inhibiting manufacture of an aseptic package.

To avoid this, according to prior art, a cleaning in place (CIP) system is provided as means for sterilizing the interior of the blow molding machine after the blow molding machine is opened. The CIP system can clean a valve block that controls blow air or the like or other components without disassembly of the blow molding machine (see Patent Document 2, for example).

Furthermore, it is proposed to clean the interior of a blow molding die by opening the die and blasting a cleaner onto the inner wall surface of the die from a cleaning nozzle or to clean the interior of a die by injecting a cleaner into the die from an extension rod (see Patent Documents 3 and 4, for example).

PRIOR ART DOCUMENT

Patent Document

Patent Document 1: Japanese Patent Laid-open Publication No. 2000-326935
Patent Document 2: Japanese Patent Laid-open Publication No. 2010-274651
Patent Document 3: Japanese Patent Laid-open Publication No. 2011-42169
Patent Document 4: Japanese Patent Laid-open Publication No. 2011-51337

Problems to be Solved by the Invention

The conventional CIP system and the method of injecting a cleaner into a die from an extension rod have a problem that a large-scale apparatus is required to circulate the cleaner.

The method of injecting a cleaner into a die serving as a molding die form an extension rod and the method of opening a die and injecting a cleaner to the inner wall surface of the die from a cleaning nozzle have a problem that a holding member, such as a mandrel or a gripper, that holds a preform during heating or molding of the preform cannot be sterilized. In addition, the interior of the blow molding machine needs to be dried after the cleaning, and the drying step requires a long time and a large amount of energy, so that the availability of the blow molding machine is substantially reduced. In addition, the conventional blow molding machine needs to be modified to have a more sanitary structure to ensure the ease of cleaning and needs to have an additional sealing structure to prevent leakage of the cleaner.

An object of the present invention is to solve the problems described above.

Means for Solving the Problems

To attain the object described above, the present invention adopts the configurations described below.

Note that reference symbols in parentheses are given to facilitate understanding of the present invention and are not intended to limit the scope of the present invention.

Specifically, the invention according to a first embodiment adopts a method for sterilizing a blow molding machine, wherein a preform (1) is filled with a liquid sterilizer (P) containing an ethanol constituent or both an ethanol constituent and a hydrogen peroxide constituent, and blow air is blasted into the preform (1) in a state where the liquid sterilizer (P) remains in the preform (1) to diffuse the liquid sterilizer (P) in the blow molding machine.

The invention according to another embodiment adopts a method for sterilizing a blow molding machine that sterilizes the blow molding machine by filling a preform (1) with a liquid sterilizer and blasting blow air into the preform (1) in a state where the liquid sterilizer remains in the preform (1) to diffuse the liquid sterilizer (P), wherein the preform (1) containing the liquid sterilizer is held by a holding member (9) and heated to activate the liquid sterilizer (P) in the preform (1), the holding member (9) is sterilized by the activated sterilizer, the preform (1) is then put in a molding die (13), an extension rod (15) is made to protrude into the preform (1), blow air is blasted into the preform (1) from a valve block (14) to expand the preform (1) into a container (2) and at the same time diffuse the remaining liquid sterilizer (P) in the container (2), the extension rod (15) then retracts, and the sterilizer remaining in the container (2) is guided to the retracted extension rod (15) through the valve block (14) along with the blow air.

The remaining sterilizer in the container (2) may be further guided into a chamber (19) surrounding the blow molding machine after being guided to the retracted extension rod (15) through the valve block (14) along with the blow air.

An interior of the molding die (13) of the blow molding die can also be sterilized by blasting the blow air into the preform (1) to expand and break the preform (1), thereby diffusing the remaining liquid sterilizer (P).

The preform (1) can also be blow-molded after the sterilizer is made to adhere to an outer surface of the preform (1).

The liquid sterilizer (P) can contain one or both of a hydrogen peroxide constituent and an ethanol constituent.

The invention according to another embodiment adopts a blow molding machine comprising a transfer device that transfers a preform (1) and a container (2) from where the preform (1) is supplied to the blow molding machine to where the preform (1) is molded into the container (2), a heating part (3) that heats the preform (1) to a blow molding temperature, and a blow molding die that molds the preform (1) into the container (2) by blow air, the heating part and the blow molding die being sequentially arranged from an upstream side to a downstream side along the transfer device, wherein a liquid sterilizer supplying device (20) is provided at a predetermined position, the liquid sterilizer supplying device (20) supplying a liquid sterilizer (P) containing an ethanol constituent or both an ethanol constituent and a hydrogen peroxide constituent into the preform (1) before the preform (1) reaches the molding die (13), and in sterilization of the blow molding machine, the liquid sterilizer is supplied into the preform by the liquid sterilizer supplying device (20), and the preform (1) containing the liquid sterilizer is blow-molded in the molding die (13).

Another embodiment is a blow molding machine comprising a transfer device that transfers a preform (1) and a container (2) from where the preform (1) is supplied to the blow molding machine to where the preform (1) is molded into the container (2), a heating part (3) that heats the preform (1) to a blow molding temperature, and a molding die (13) that molds the preform (1) into the container (2) by blow air, the heating part and the blow molding die being sequentially arranged from an upstream side to a downstream side along the transfer device, a liquid sterilizer supplying device (21) may be provided at a predetermined position, the liquid sterilizer supplying device supplying a liquid sterilizer (P) into the preform (1) before the preform (1) reaches the molding die (13), a valve block (14) may be provided adjacent to the molding die (13), an extension rod (15) capable of protruding into and retracting from the molding die (13) may be provided through the valve block (14), a housing box (26) capable of housing the extension rod (15) when the extension rod retracts may be provided adjacent to the valve block (14), and in sterilization of the blow molding machine, when the liquid sterilizer (P) is supplied into the preform (1) by the liquid sterilizer supplying device (21), and the preform (1) containing the liquid sterilizer (P) is heated and put in the molding die (13), the motor (25) may rotate in a forward direction to make the extension rod (15) protrude into the preform (1), and the blow air may be blasted into the preform (1) from the valve block (14) to expand the preform (1) into the container (2) and diffuse the liquid sterilizer (P) in the preform (1) in the container (2), and when the extension rod (15) retracts from the molding die (13) into the housing box (26), the sterilizer remaining in the container (2) may be guided into the housing box (26) through the valve block (14) along with the used blow air.

The housing box (26) may be provided with a ventilation part (27), and the sterilizer remaining in the container (2) may be guided into a chamber (19) surrounding the blow molding machine through the ventilation part (27) after being guided into the housing box (26) through the valve block (14) along with the blow air.

The liquid sterilizer supplying device (20) may be provided at a position where the preform (1) is yet to enter the heating part (3).

The liquid sterilizer supplying device (20) may be provided in the heating part (3).

The liquid sterilizer supplying device (20) may be provided at a position where the preform (1) has exited the heating part (3) and is yet to reach the molding die (13).

A plurality of liquid sterilizer supplying devices (20) may be provided at different positions between the position where the preform (1) is yet to enter the heating part (3) and the position where the preform (1) reaches the molding die (13).

The liquid sterilizer supplying device (21) may be capable of making the sterilizer adhere to an outer surface of the preform (1).

The sterilizer supplied from the liquid sterilizer supplying device (20) may contain one or both of a hydrogen peroxide constituent and an ethanol constituent.

Effects of the Invention

According to the present invention, a blow molding machine can be simply sterilized without the conventional CIP system or the extension rod having a cleaner injection nozzle. In addition, since the interior of the blow molding machine can be sterilized without disassembling the blow molding machine, the interior of the blow molding machine can be sterilized at a desired time while containers such as the bottles (2) are continuously molded.

In the present invention, if the sterilizer is supplied into the preform (1) before the preform (1) is heated or during heating of the preform (1), the holding member (9) holding the preform (1) can also be sterilized.

In the present invention, if the interior of the molding die (13) is also sterilized by blasting blow air into the preform (1) from the valve block (14) to expand and break the preform (1) to diffuse the remaining liquid sterilizer (P), sterilization of the interior of the molding die (13) can be achieved without making the sterilizer adhere to the outer surface of the preform (1).

In the present invention, if the sterilizer is made to adhere to the outer surface of the preform (1), the interior of the molding die (13) can also be sterilized.

EMBODIMENTS FOR CARRYING OUT THE INVENTION

In the following, embodiments of the present invention will be described.

<First Embodiment>

Figure 1:
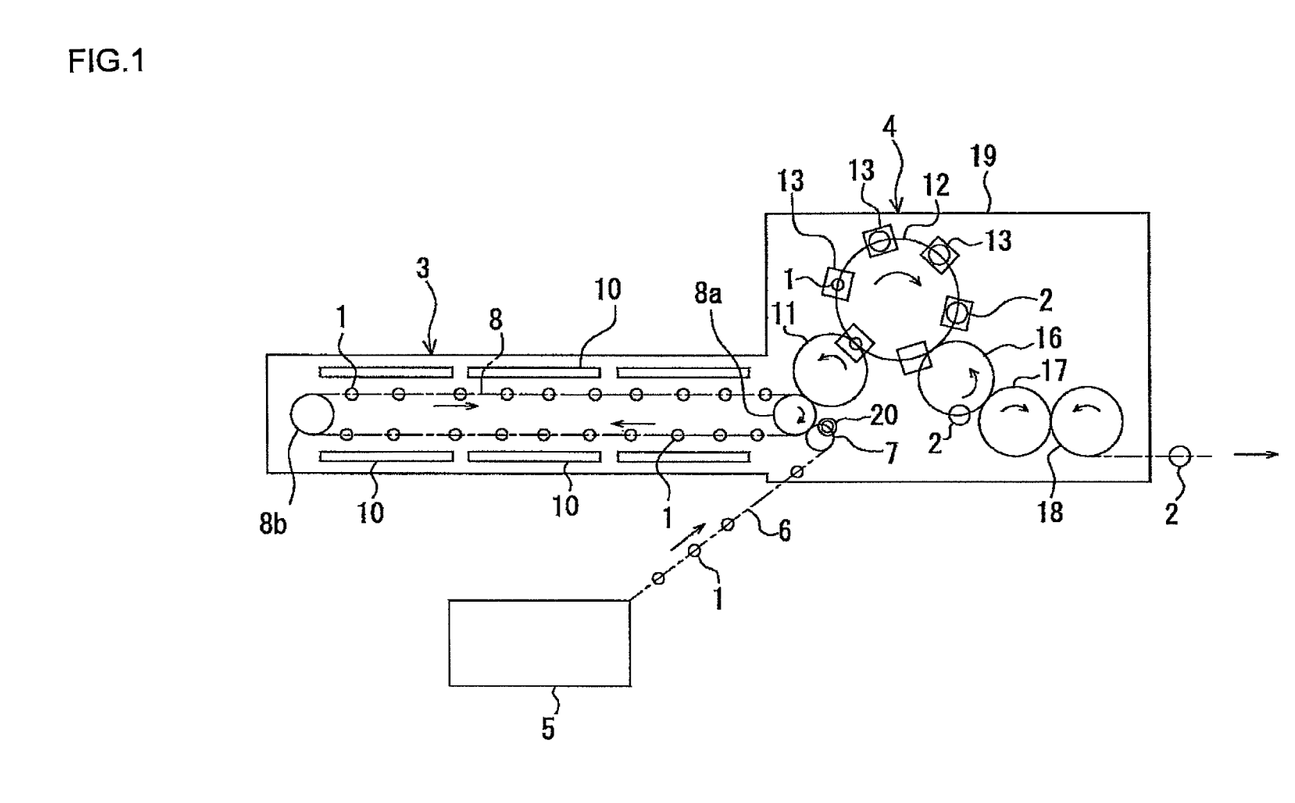
FIG. 1 is a schematic plan view of a blow molding machine according to a first embodiment of the present invention.
Figure 2A:
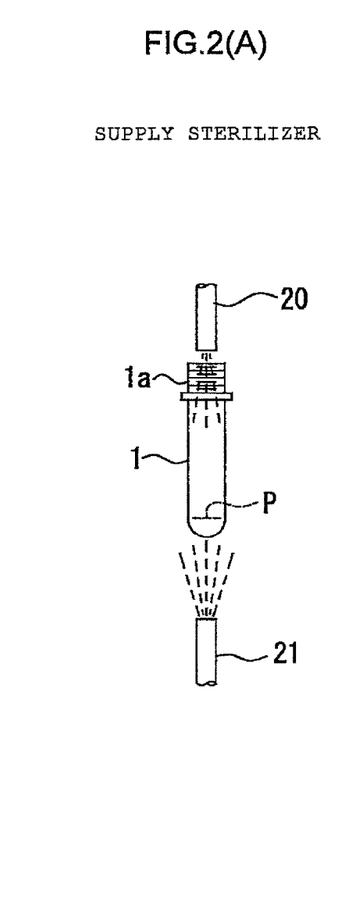
FIG. 2 includes diagrams for illustrating different steps of a sterilization method performed by the blow molding machine.
Figure 2B:
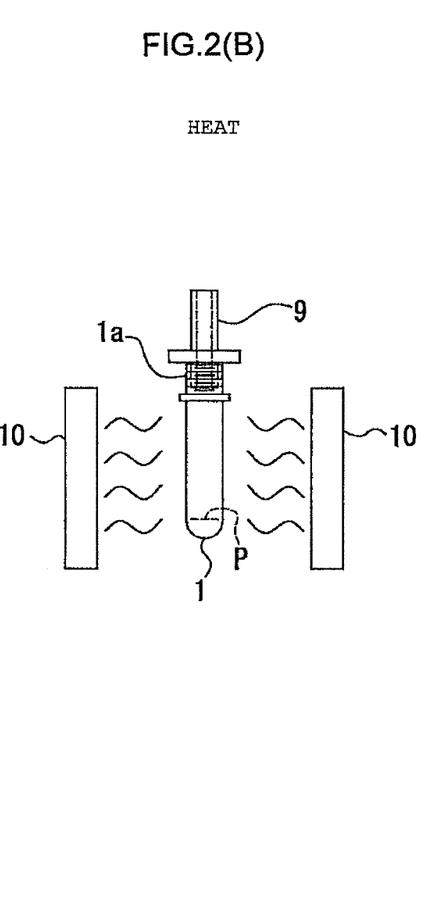
Figure 2C:
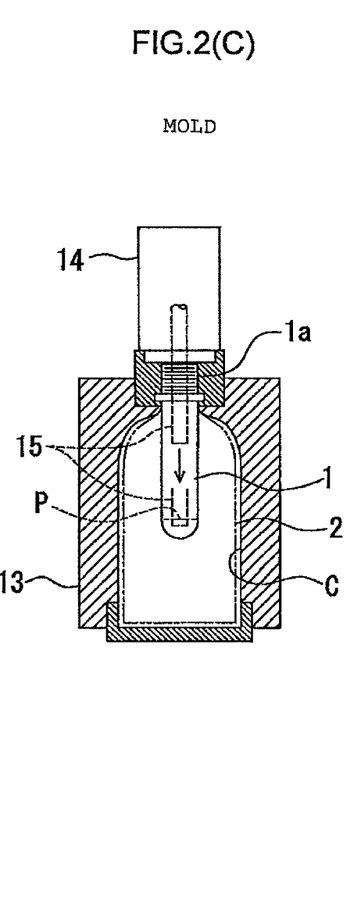

As shown in FIG. 1, a blow molding machine has a transfer device that transfers a bottomed tubular preform 1 (see FIG. 2(A)) and a bottle 2 (see FIG. 2(C)) from a stage where the preform 1 is supplied to a stage where the preform 1 is molded into the bottle 2. In the blow molding machine, a heating part 3 in which the preform 1 is heated to a blow molding temperature and a molding part 4 in which the preform 1 is molded into the bottle 2 by blow air are provided in this order from an upstream side to a downstream side along the transfer device.

The heating part 3 and the molding part 4 are covered with a chamber 19, which serves as a protective cover. In the chamber 19, a positive pressure is maintained by constantly suppling an aseptic air into the chamber 19 from an aseptic air supply source (not shown).

On the upstream side of the transfer device, there is provided a preform supplying machine 5 that successively supplies preforms 1 at predetermined intervals.

Figure 3:
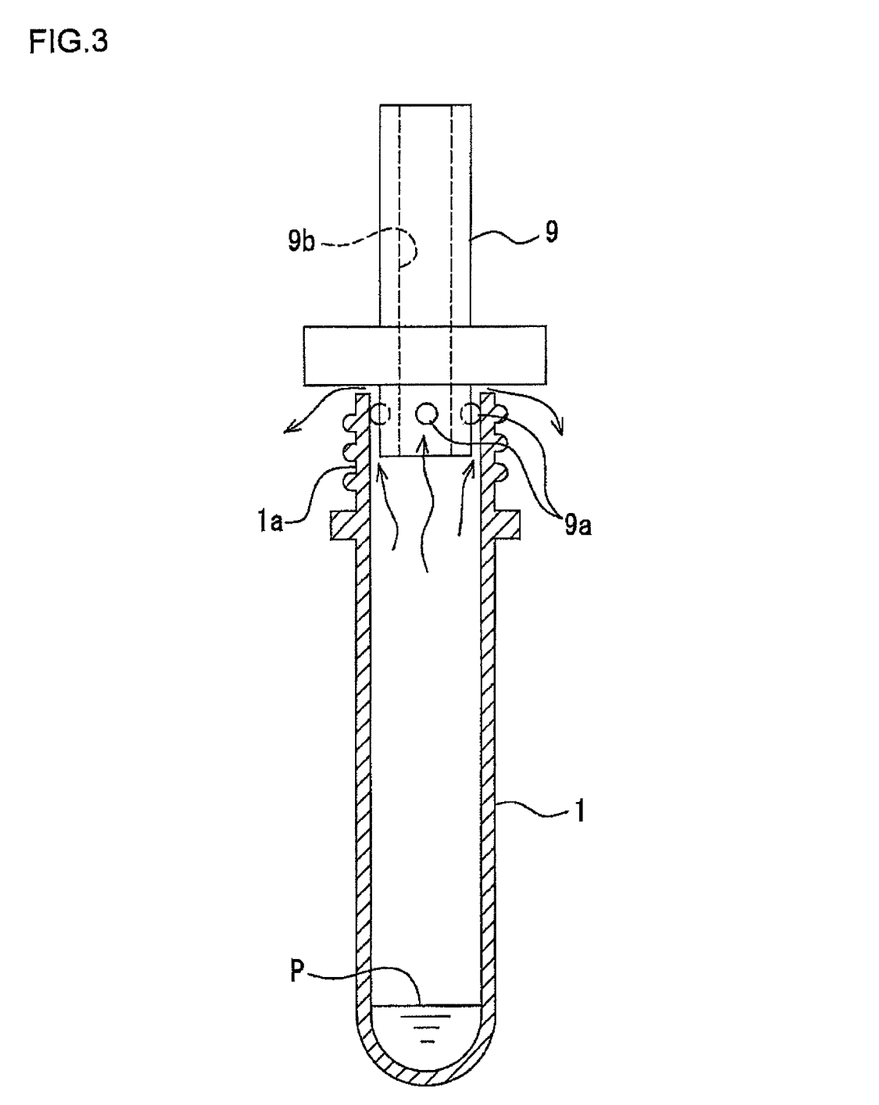
FIG. 3 is a partial cross-sectional view of a preform held by a holding member.

As shown in FIG. 3, the preform 1 is a bottomed tubular body similar to a test tube and is formed from polyethylene terephthalate (PET), for example, by injection molding or the like. The preform 1 will be eventually shaped by blow molding into the bottle 2, which is a container. However, a mouth portion 1a, a male thread and the like similar to those of the finished bottle 2 are formed on the preform 1 in the early stage of the molding of the preform 1.

An endless conveyor 6, which is a delivery device for the preform 1, extends from the preform supplying machine 5 to the blow molding machine.

The heating part 3 is disposed in a part of the blow molding machine where the blow molding machine receives the preforms 1 from the preform supplying machine 5.

The endless conveyor 6 extends into the heating part 3 and is provided with a wheel 7 at its end in the heating part 3. The endless conveyor 6 and the wheel 7 are provided with a gripper or the like (not shown) that holds the preform 1 during conveyance.

The heating part 3 has a furnace chamber that is elongated in one direction. In the furnace chamber, an endless chain 8 serving as a transfer device for the preforms extends between a pair of pulleys 8a and 8b that are disposed to be opposed to each other in a horizontal plane. The endless conveyor 6 is attached to the pulley 8a disposed close to an inlet port of the furnace chamber.

A large number of holding members 9 for preforms 1 like that shown in FIG. 3 are attached to the endless chain 8 at regular intervals. Each holding member 9 can rotates on its axis while moving with the endless chain 8. As shown in FIG. 3, the holding member 9 is formed as a spindle and has a plurality of ball-shaped elastic bodies 9a embedded in an outer surface of a lower part thereof. Once the holding member 9 is inserted into the mouth portion 1a of the preform 1, the elastic bodies 9a are elastically deformed to hold the preform 1 on the holding member 9.

The holding member 9 is inserted into the mouth portion 1a of the preform 1 passed from the wheel 7 to the endless chain 8 as shown in FIGS. 2(B) and 3, and thus, the preform 1 is held in an upright position by the holding member 9.

If the holding member 9 is formed as a mandrel rather than the spindle, the preform 1 can be supported in an inverted position during conveyance.

A heater 10 that emits infrared rays is attached to an inner wall surface of the furnace chamber of the heating part 3 along a forward and a return run of the endless chain 8.

After the preform 1 is received by the holding member 9 via the endless conveyor 6 and the wheel 7, the preform 1 travels along the inner wall surface of the heating part 3 while rotating on its axis. The preform 1 conveyed by the holding member 9 is heated by the heater 10 provided over the inner wall surface of the heating part 3. When the preform 1 is travelling in the heating part 3, the preform 1 rotates on its axis as the holding member 9 rotates, and is uniformly heated by the heater 10 so that the preform 1 excluding the mouth portion 1a is heated to 90° C. to 130° C., which is a temperature range suitable for blow molding. The temperature of the mouth portion 1a is kept to be equal to or lower than 70° C., at which no deformation or the like occurs, so that sealing between the mouth portion 1a and a cap (not shown) to be fitted on the mouth portion 1a is not compromised.

At a connection of the pulley 8a at one end of the endless chain 8 to the return run of the endless chain 8, there is provided a row of wheels 11 and 12 that receive the preform 1 heated by the heater 10 and convey the preform 1 into the molding part 4.

The upstream wheel 11 is provided with a gripper (not shown) on the circumference thereof, and the gripper grasps the preform 1 at the mouth portion 1a thereof and conveys the preform 1 to the following downstream wheel 12.

The downstream wheel 12 is provided with a plurality of two-piece blow molding dies 13 on the circumference thereof, at predetermined intervals, and the blow molding die 13 receives the heated preform 1 from the gripper of the upstream wheel 11 and molds the preform 1 into the bottle 2 by blow air. The blow molding dies 13 rotate at a constant velocity around the wheel 12 as the wheel 12 rotates.

As shown in FIG. 2(C), a valve block 14 is removably coupled to each blow molding die 13. The valve block 14 is mainly intended to control supply, discharge or the like of the blow air, and an extension rod 15 is vertically slidably provided in the valve block 14.

Once the blow molding die 13 receives the heated preform 1 from the wheel 11, the die 13 is closed to mold the preform 1 into the bottle 2 while rotating with the valve block 14. In the blow molding, as shown in FIG. 2(C), the extension rod 15 lowers in the valve block 14 and comes into contact with the inner bottom of the preform 1 to stretch the preform 1, and then, an aseptic blow air is blasted into the preform 1 from an annular nozzle (not shown) formed between the extension rod 15 and the valve block 14. Since the preform 1 has already been heated to a predetermined temperature in the heating part 3, the preform 1 is smoothly blow-molded into the bottle 2.

The blow molding die 13 rotates with the wheel 12 and is opened to release the molded bottle 2 at a position where the blow molding die 13 is adjacent to a conveyance wheel 16. The bottle 2 is received by a gripper (not shown) of the conveyance wheel 16.

Another row of wheels 17 and 18 is coupled to the conveyance wheel 16, and the preform 1 is conveyed to the outside of the blow molding machine by grippers of the wheels 17 and 18.

As described above, the blow molding machine is opened for repair, maintenance or other purposes, and the interior of the blow molding machine opened and contaminated has to be sterilized.

To this end, a liquid sterilizer supplying device that supplies a liquid sterilizer P into the preform 1 as shown in FIGS. 2(A) and 3 before the preform 1 reaches the blow molding die 13 is provided at a predetermined position in the blow molding machine.

In FIG. 1, reference numeral 20 denotes a sterilizer supplying nozzle, which is the liquid sterilizer supplying device, and the sterilizer supplying nozzle is disposed around the wheel 7 at a position where the preform 1 is yet to enter the heating part 3. As shown in FIG. 2(A), the sterilizer supplying nozzle 20 is disposed so that a nozzle hole at a lower end thereof is directly opposed to the mouth portion 1a of the preform 1 grasped by the gripper (not shown). The sterilizer supplying nozzle 20 can be opened and closed by a valve (not shown) and dispenses a predetermined amount of the liquid sterilizer P into one preform 1 each time the sterilizer supplying nozzle 20 is opened and closed.

As shown in FIG. 2(A), another sterilizer supplying nozzle 21 directly opposed to the bottom of the preform 1 is provided as required. A sterilizer discharged from the sterilizer supplying nozzle 21 adheres to the outer surface of the preform 1 in the form of a uniform coating film.

Next, an operation of the blow molding machine described above will be described.

In a normal bottle molding operation, the preform 1 is conveyed into the heating part 3 of the blow molding machine by the endless conveyor 6 of the preform supplying machine 5.

Once the preform 1 is introduced into the heating part 3, the preform 1 is held by the holding member 9 attached to the endless chain 8 and heated to a temperature suitable for blow molding by the heater 10 while traveling with the moving endless chain 8 (see FIG. 2(B)).

The preform 1 heated to a predetermined temperature is passed from the holding member 9 of the endless chain 8 to the gripper of the wheel 11 and then received in the blow molding die 13 rotating with the wheel 12.

Once the blow molding die 13 receives the preform 1 and is closed, the extension rod 5 lowers from inside the valve block 14 into the preform 1 to the bottom thereof, thereby stretching the preform 1. Then, the blow air is blasted into the preform 1 from the annular nozzle between the valve block 14 and the extension rod 15, and the preform 1 is molded into the bottle 2 in a cavity C of the blow molding die 13 (see FIG. 2(C)).

Once the preform 1 is molded into the bottle 2 and the blow molding die 13 reaches a position where the blow molding die 13 is adjacent to the conveyance wheel 16, the blow molding die 13 is opened to release the molded bottle 2.

The released bottle 2 is received by the gripper (not shown) of the conveyance wheel 16 and conveyed to the outside of the blow molding machine.

As described above, some failure can occur in the blow molding machine during manufacture of the bottles 2 by the blow molding machine. In such a case, an operator stops the blow molding machine, opens the chamber 19 covering the blow molding machine, and opens the blow molding die 13 or the like to inspect or clean the interior thereof.

If the blow molding machine is opened, microorganisms from the external environment including a human body enter the blow molding machine, adhere to the molding die 13, the extension rod 15 or the like and also to the preform 1 or the bottle 2, thereby inhibiting manufacture of an aseptic package. To avoid this, before the blow molding machine is restarted, the interior of the blow molding machine needs to be sterilized.

To this end, when inspection or the like of the interior of the blow molding machine is completed, and the blow molding machine is restored to its original state, the liquid sterilizer P is first supplied into the preform 1 as shown in FIG. 2(A).

In the first embodiment, before the preform 1 enters the heating part 3, such as when the preform 1 is traveling around the wheel 7, a predetermined amount of liquid sterilizer P is supplied into the preform 1 from the sterilizer supplying nozzle 20.

The liquid sterilizer P may contain one or both of hydrogen peroxide and ethanol. As an alternative, peracetic acid, a sodium hypochlorite solution, or an acidic water is effective.

When the liquid sterilizer P contains hydrogen peroxide, the concentration of the hydrogen peroxide solution is preferably 0.1% by weight to 35% by weight, or more preferably 1% by weight to 5% by weight.

When the liquid sterilizer P contains an ethanol constituent, the sterilizer can be efficiently vaporized in the blow molding machine.

The amount of the liquid sterilizer P supplied into the preform 1 is 0.01 mL to 10 mL for each preform, or desirably 0.1 mL to 1mL for each preform.

As shown in FIG. 2(A), when the liquid sterilizer P is supplied into the preform 1 from the sterilizer supplying nozzle 20, the sterilizer may be injected from the sterilizer supplying nozzle 21 disposed below the preform 1 so that the sterilizer adheres to the outer surface of the preform 1, as required.

The preform 1 containing the liquid sterilizer P is then held by the holding member 9, introduced into the heating part 3 and heated by the heater 10 from the outer surface side thereof (see FIG. 2(B)). The preform 1 is heated to a blow molding temperature as the preform 1 passes through the heating part 3.

As a result of being heated in the heating part 3, some of the liquid sterilizer P in the preform 1 is vaporized or otherwise activated, and the activated sterilizer flows to the gap between the mouth portion 1a of the preform 1 and the holding member 9 (see FIG. 3). As a result, a part of the holding member 9 that is in contact with the preform 1, in particular, the elastic bodies 9a and their surroundings, is appropriately sterilized by the gas of the sterilizer.

The preform 1 conveyed out of the heating part 3 is still held by the holding member 9, put in the molding die 13 that is now separated into two halves, and confined in the molding die 13 when the molding die 13 is clamped. After the clamping, the valve block 14 is connected to an upper end of the molding die 13. At this stage, constituents of the liquid sterilizer P remain in the preform 1 (see FIG. 2(C)).

By controlling the valve block 14, the extension rod 15 moves downward through the valve block 14 and enters the preform 1. The extension rod 15 stretches the preform 1 as the extension rod 15 enters preform 1. In this process, a tip end of the extension rod 15 comes into contact with the liquid sterilizer P remaining in the preform 1 and is thereby sterilized (see FIG. 2(C)).

After that, the blow air is blasted into the preform 1 from the valve block 14 to expand the preform 1. As a result, the preform 1 is shaped into the bottle 2, which is a container, as shown by the alternate long and two short dashes line in FIG. 2(C).

In addition, as a result of the blow air being blasted into the preform 1, constituents of the liquid sterilizer P remaining in the preform 1 is scattered and diffused. The diffused sterilizer adheres to and sterilizes the inner surface of the molded bottle 2 and the outer part of the extension rod 15.

After that, by controlling the valve block 14, the blow air is discharged from the valve block 14, and the interior of the valve block 14 and the extension rod 15 are sterilized by the sterilizer contained in the discharged blow air.

This sterilization process for the interior of the blow molding machine can be performed each time one bottle 2 is molded in one molding die 13 or each time a plurality of bottles 2 are molded in one molding die 13.

After the sterilization process for the interior of the blow molding machine is thus completed, supply of the liquid sterilizer P from the sterilizer supplying nozzle 20 into the preform 1 is stopped, and molding of bottles 2 is continued.

Figure 4:
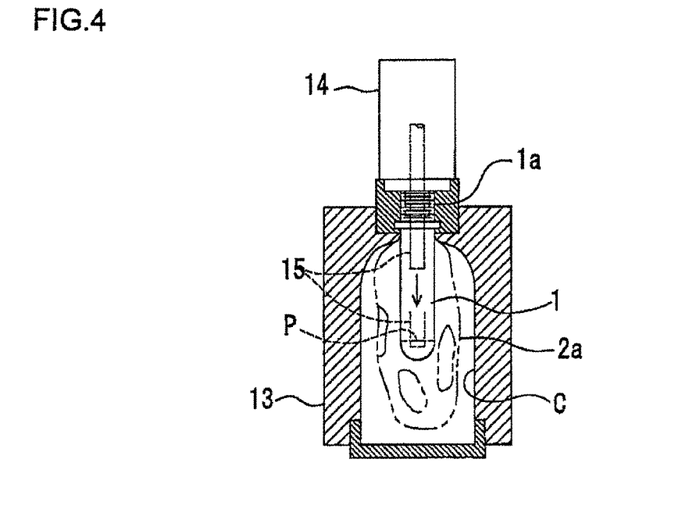
FIG. 4 is a diagram for illustrating a modification of the step shown in FIG. 2(C).

In the step of molding the preform 1 shown in FIG. 2(C), the blow air can be blasted into the preform 1 through the valve block 14 not only to expand the preform 1 but also break or damage the preform 1, as shown in FIG. 4. In FIG. 4, reference numeral 2a denotes a defective bottle that is broken, deformed or perforated. This can be achieved by increasing the amount of liquid sterilizer P supplied into the preform 1 or blasting the blow air into the preform 1 more rapidly or under higher pressure, for example.

If the preform 1 is broken in the course of expansion in this way, the liquid sterilizer P remaining in the preform 1 is scattered and diffused in the molding die 13 to adhere the inner surface of the molding die 13, so that a larger part including the cavity C can be sterilized.

In this case again, the sterilization process for the interior of the blow molding machine can be performed each time one bottle 2 is molded in one molding die 13 or each time a plurality of bottles 2 are molded in one molding die 13.

After the sterilization process for the interior of the blow molding machine is thus completed, molding of bottles 2 is continued.

<Second Embodiment>

Figure 5:
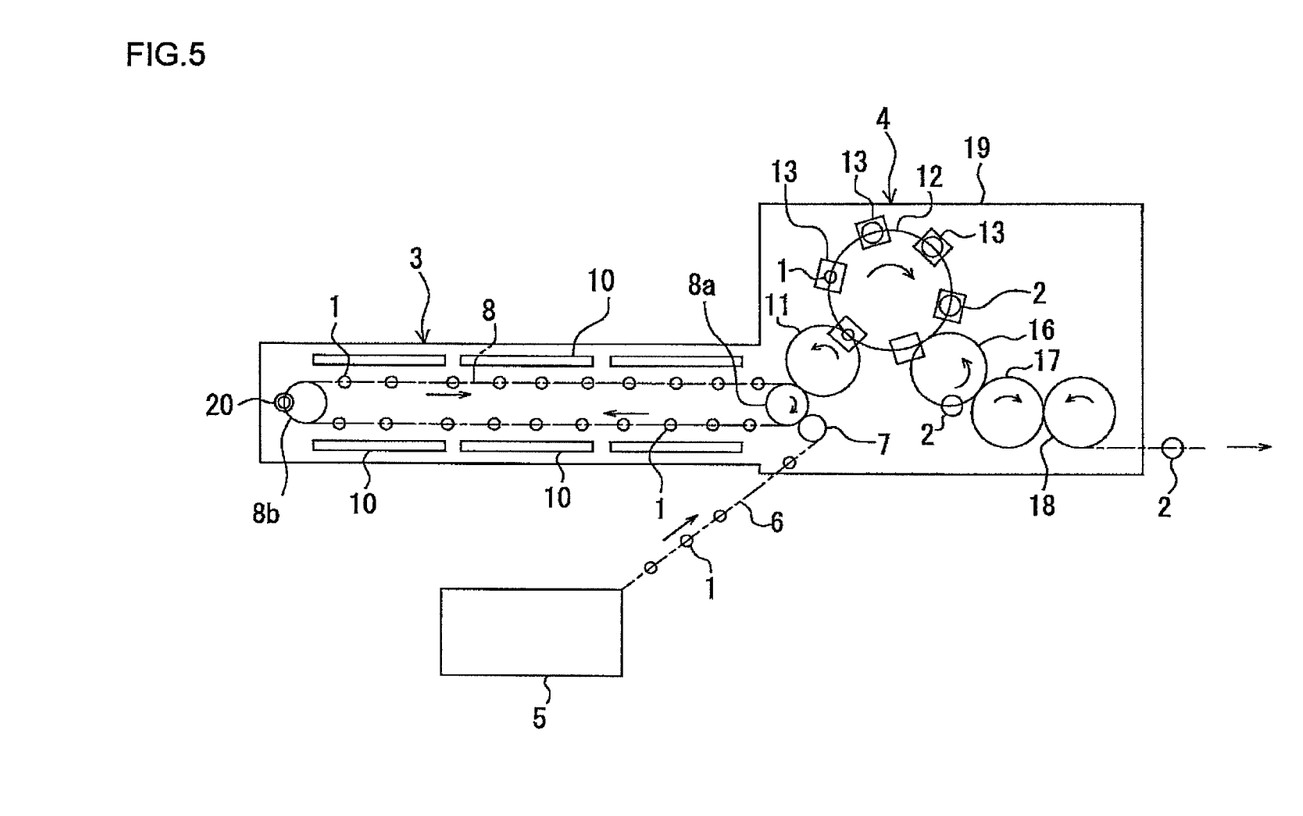
FIG. 5 is a schematic plan view of a blow molding machine according to a second embodiment of the present invention.

As shown in FIG. 5, according to a second embodiment, the sterilizer supplying nozzle 20 is disposed approximately at the middle of the path of the preform 1 in the heating part 3. More specifically, the sterilizer supplying nozzle 20 is disposed to be directly opposed to the mouth portion 1a of the preform 1 held by the holding member 9 in the vicinity of the pulley 8b, which is one of the pair of pulleys 8a and 8b around which the endless chain 8 is wound that is disposed at the depth of the heating part 3.

In this case, since the preform 1 is held by the holding member 9 as shown in FIG. 3, the liquid sterilizer P discharged from the sterilizer supplying nozzle 20 flows into the preform 1 through a through-hole 9b that penetrates the holding member 9 at the center thereof. Alternatively, the sterilizer supplying nozzle 20 is inserted into the through-hole 9b of the holding member 9 to supply the liquid sterilizer P into the preform 1.

As required, as shown in FIG. 2(A), another sterilizer supplying nozzle 21 may be disposed so as to be directly opposed to the bottom of the preform 1.

In the second embodiment, since the sterilizer is supplied into the preform 1 that is already heated to some extent, the sterilizer is quickly vaporized, and the holding member 9 is quickly sterilized.

<Third Embodiment>

Figure 6:
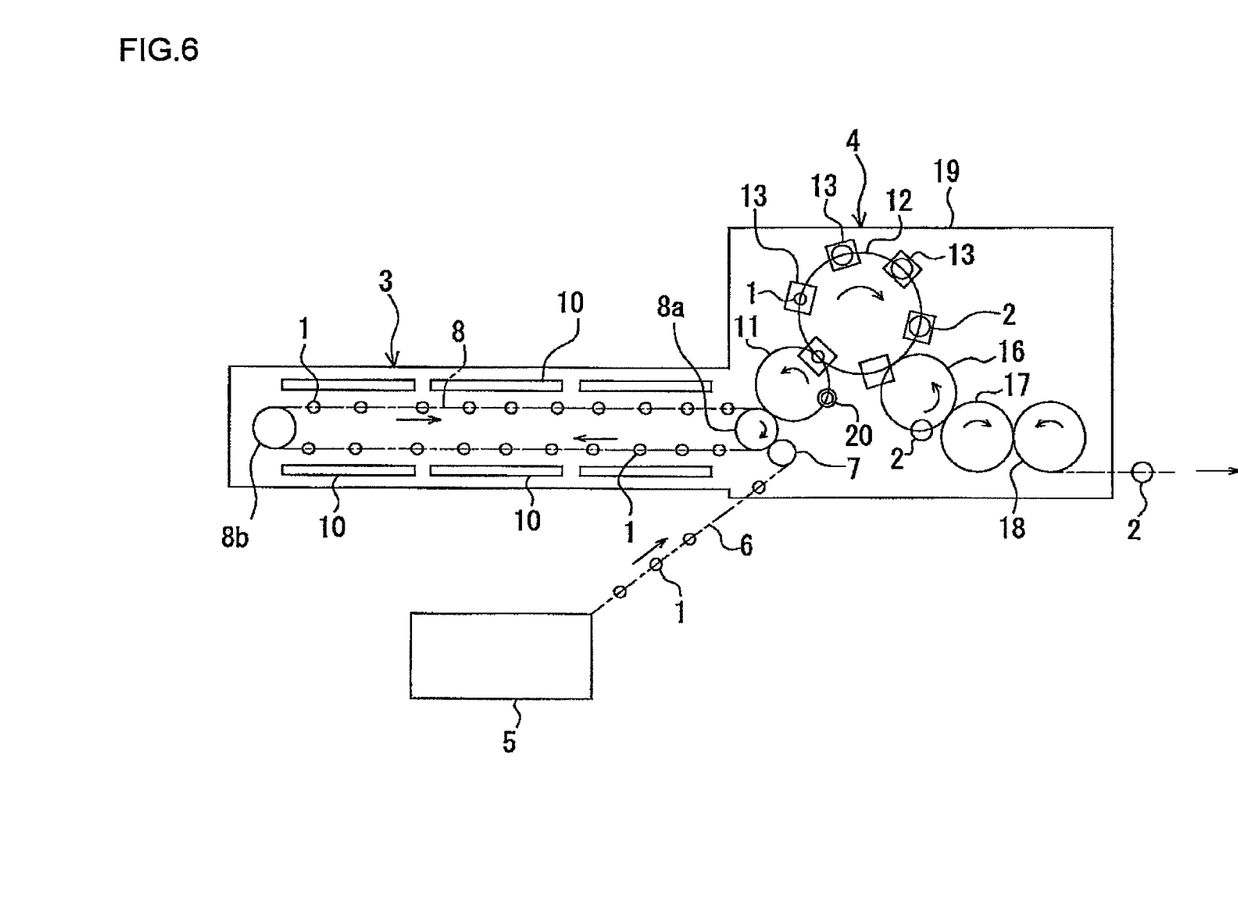
FIG. 6 is a schematic plan view of a blow molding machine according to a third embodiment of the present invention.

As shown in FIG. 6, according to a third embodiment, the sterilizer supplying nozzle 20 is disposed at a position where the preform 1 has exited the heating part 3 and is yet to reach the molding die 13. More specifically, the sterilizer supplying nozzle 20 is disposed to be directly opposed to the mouth portion 1a of the preform 1 held by the gripper (not shown) around the wheel 11 that receives the preform 1 from the endless chain 8 (see FIG. 2(A)).

In addition, as required, as shown in FIG. 2(A), another sterilizer supplying nozzle 21 may be disposed so as to be directly opposed to the bottom of the preform 1.

<Fourth Embodiment>

Figure 7:
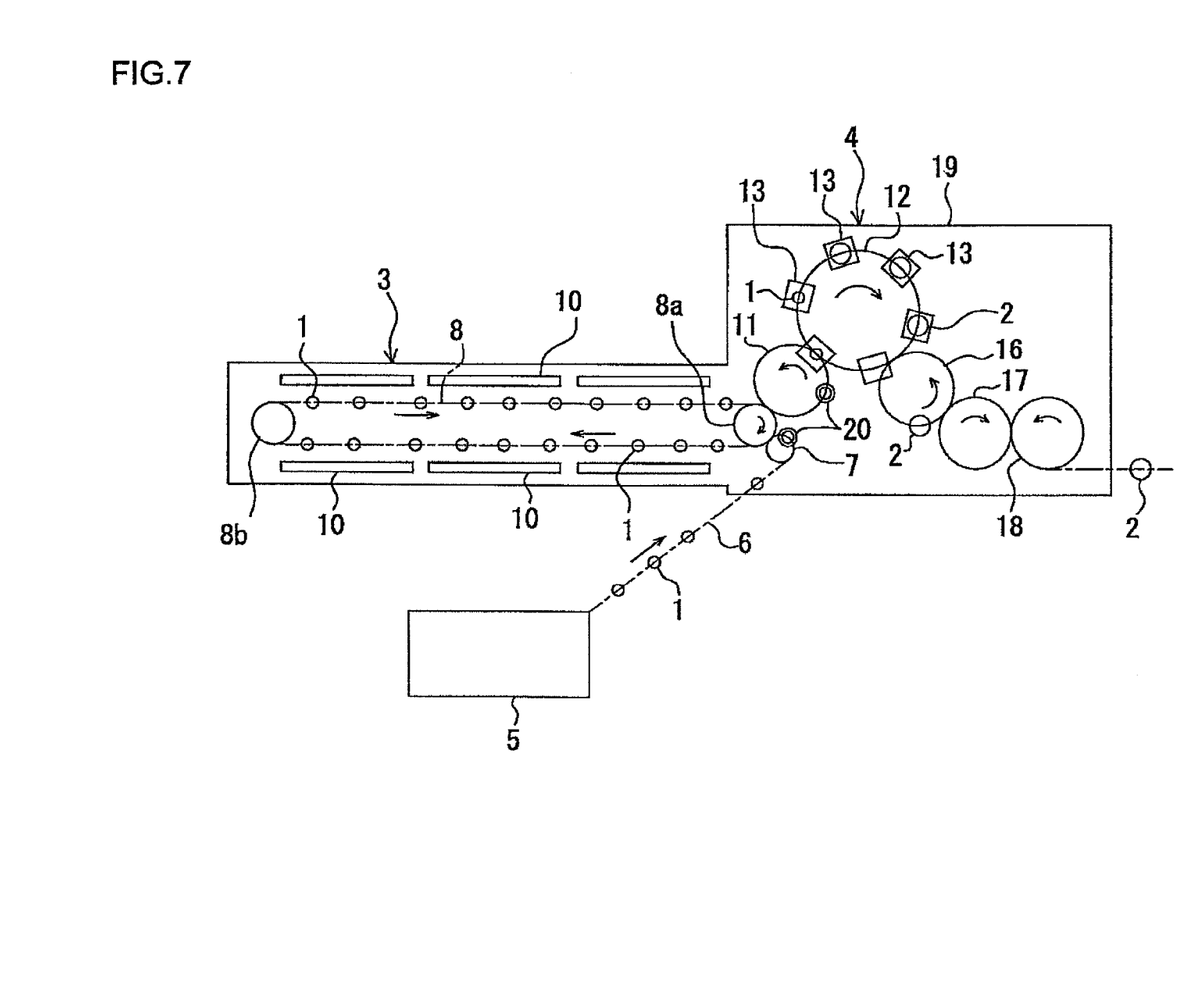
FIG. 7 is a schematic plan view of a blow molding machine according to a fourth embodiment of the present invention.

As shown in FIG. 7, according to a fourth embodiment, sterilizer supplying nozzles 20, 20 are disposed at a position where the preform 1 is yet to enter the heating part 3 as with the position according to the first embodiment and at a position where the preform 1 has exited the heating part 3 and is yet to reach the molding die 13 as with the position according to the third embodiment.

If the sterilizer supplying nozzles 20, 20 are disposed in this way, even if the liquid sterilizer P supplied from the sterilizer supplying nozzle 20 on the upstream side is consumed in the heating part 3, the liquid sterilizer P can be replenished from the sterilizer supplying nozzle 20 on the downstream side.

In addition, as required, as shown in FIG. 2(A), another sterilizer supplying nozzle 21 may be disposed so as to be directly opposed to the bottom of the preform 1.

<Fifth Embodiment>

Figure 8:
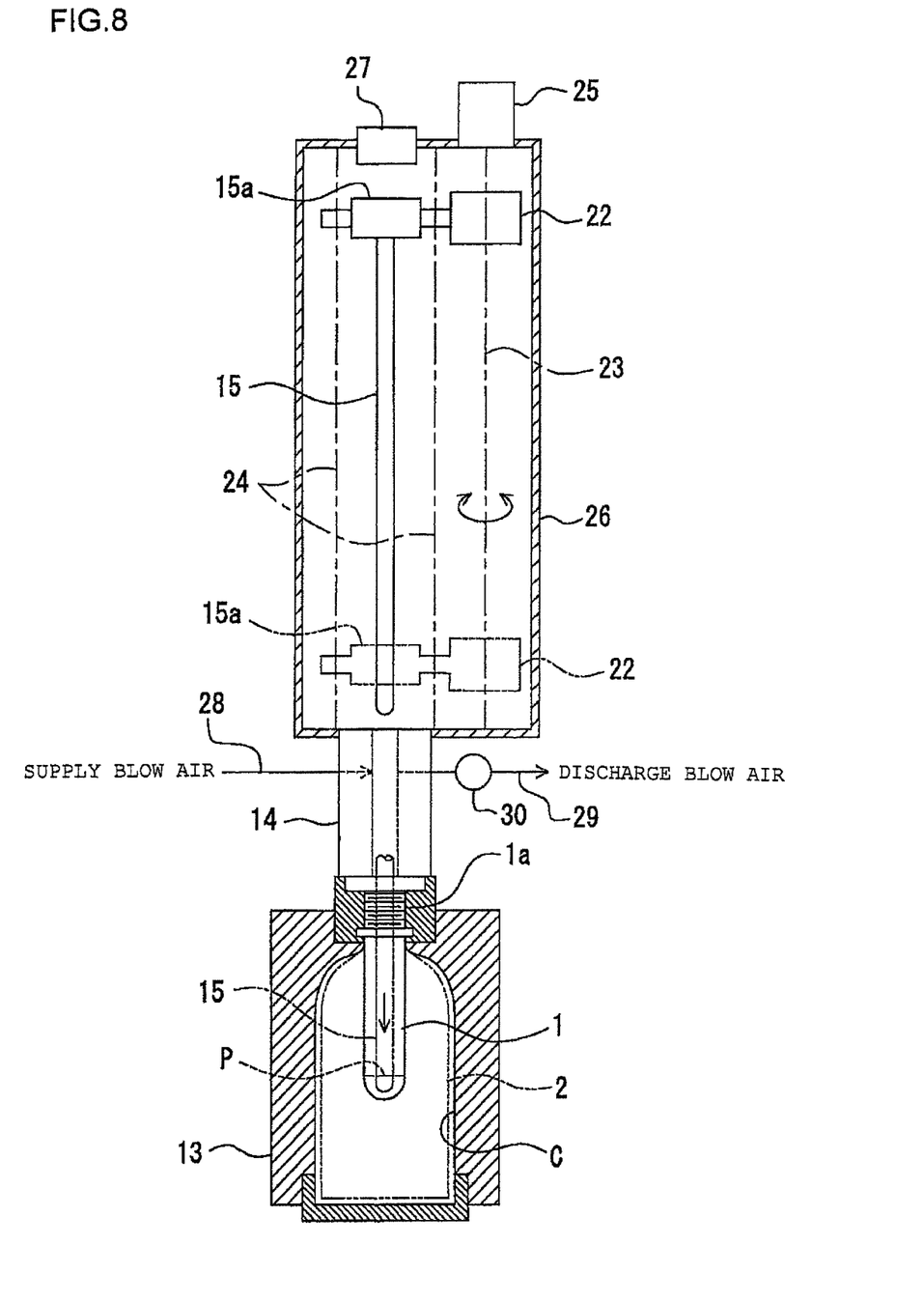
FIG. 8 is a schematic vertical cross-sectional view of a molding die in a blow molding machine according to a fifth embodiment of the present invention.

As shown in FIG. 8, the valve block 14 is provided adjacent to the molding die 13 in the blow molding machine.

Piping 28 for supplying blow air through a predetermined valve (not shown) therein and piping 29 for discharging used blow air through another valve (not shown) are connected to the valve block 14. The discharging piping 29 is provided with a silencer 30.

In addition, the extension rod 15 that penetrates the valve block 14 and can protrude into and retract from the molding die 13 is provided. The extension rod 15 is disposed in such a manner that the central axis thereof is aligned with the extension of the central axis of the molding die 13 and the central axis of the preform 1 held in the molding die 13.

A driving part that makes the extension rod 15 perform the protrusion and retraction operations described above is provided for the extension rod 15. More specifically, a nut 22 is coupled to a rear end of the extension rod 15, and a feeding threaded bar 23 that extends in parallel with the extension rod 15 is screwed into the nut 22. In order to make the extension rod 15 precisely perform the protrusion and retraction operations described above, a guide member 24 that extends in parallel with the feeding threaded bar 23 is provided. One or more rail-shaped or bar-shaped guide members 24 are provided, and the guide members 24 are slidably engaged with a base portion 15a of the extension rod 15 at the rear end thereof or with the nut 22.

The feeding threaded bar 23 is coupled to an output shaft of a servomotor 25 at one end thereof and thus can be rotated in both forward and reverse directions.

The extension rod 15, the feeding threaded bar 23 that is part of the driving part therefor and the like are covered by and sealed in a housing box 26. The housing box 26 may be divided by a partition wall (not shown) into a section that houses the extension rod 15 and a section that houses the feeding threaded bar 23.

Reference numeral 27 denotes a ventilation part that includes a filter or the like through which any remaining sterilizer P filling the housing box 26 passes to the outside of the housing box 26 along with the used blow air. The sterilizer P flowing with the blow air is caught and decomposed by the filter of the ventilation part 27, and only the blow air flows out of the housing box 26.

The ventilation part 27 may be a simple ventilation hole, rather than including a filter, and any remaining sterilizer P filling the housing box 26 may be guided into the chamber 19 outside the housing box 26 along with the used blow air so that the interior of the chamber 19 can also be sterilized by the sterilizer P.

Next, an operation of the blow molding machine according to the fifth embodiment will be described.

In the blow molding machine described above, if a desired liquid sterilizer P such as hydrogen peroxide is put in the preform 1 (see FIG. 2(A)), and the preform 1 held by the holding member 9 is heated (see FIG. 2(B)), some of the liquid sterilizer P in the preform 1 is vaporized or otherwise activated, and the activated sterilizer sterilizes the holding member 9.

Once the preform 1 heated as described above and containing the remaining liquid sterilizer P that has not been vaporized is put in the molding die 13, the servomotor 25 rotates in the forward direction to make the extension rod 15 protrude into the preform 1. Once the protrusion is completed, an opening of the valve block 14 is closed with a valve (not shown) provided on the extension rod 15 at the middle thereof.

Then, the blow air is blasted into the preform 1 through a predetermined valve in the valve block 14 from the piping 28 for supplying blow air, thereby expanding the preform 1 into the bottle 2, which is a container. Meanwhile, the sterilizer P is diffused in the bottle 2. As a result, the sterilizer P adheres to a front part of the extension rod 15 and is activated by the heat of the preform 1 to sterilize the front part of the extension rod 15.

When molding of the bottle 2 is completed, the used blow air is discharged to the outside of the molding die 13 through another valve in the valve block 14 and the piping 29. In this step, the discharge air noise is reduced by the silencer 30.

The blow air discharged through the piping 29 and the silencer contains hydrogen peroxide in the form of mist, gas or a mixture thereof. This discharged air containing hydrogen peroxide flows into the chamber 19, thereby sterilizing the entire molding part 4 including the molding die 13 or the like in the chamber 19.

Once molding of the bottle 2 is completed, the servomotor 25 rotates in the reverse direction, the extension rod 15 retracts, and the valve at the middle of the extension rod 15 is separated from the opening of the valve block 14. As a result, the opening of the valve block 14 is opened, and the used blow air containing hydrogen peroxide described above also flows into the housing box 26, thereby sterilizing the entire extension rod 15 in the housing box 26, the feeding threaded bar 23 of the driving part, the inner surface of the housing box 26 and the like.

The blow air having flowed into the housing box 26 exits the housing box 26 through the ventilation part 27 and flows into the chamber 19. Thus, the molding part 4 in the chamber 19 is sterilized not only by the discharge air having passed through the silencer 30 described above but also by the discharge air having passed through the ventilation part 27.

If the bottle 2 ruptures or otherwise breaks in the molding die 13 as shown in FIG. 4, the inner surface of the molding die 13 is also sterilized by the sterilizer P scattered.

After the interior of the chamber 19 is sterilized by the hydrogen peroxide contained in the discharge air described above, aseptic air is supplied into the chamber 19 from the aseptic air supplying apparatus (not shown), thereby maintaining the aseptic condition in the chamber 19. If the sterilizer filling the preform 1 contains ethanol, propanol or isopropanol, the sterilizer is instantaneously vaporized at room temperature, so that the interior of the chamber 19 is quickly sterilized. As required, the aseptic air supplying apparatus may be provided with a heater and blast heated aseptic air into the chamber 19.

REFERENCE NUMERALS

1 preform
2 container (bottle)
9 holding member
13 molding die
14 valve block
15 extension rod
20, 21 sterilizer supplying nozzle
P liquid sterilizer

The invention claimed is:

1. A method for sterilizing a blow molding machine that sterilizes the blow molding machine by filling a preform with a liquid sterilizer and blasting blow air into the preform in a state where the liquid sterilizer remains in the preform to diffuse the liquid sterilizer, wherein the preform containing the liquid sterilizer of 0.1 mL to 10 mL is held by a holding member and heated to activate the liquid sterilizer in the preform, the holding member is sterilized by the activated sterilizer, the preform is then put in a molding die, an extension rod is made to protrude into the preform, blow air is blasted into the preform from a valve block to expand the preform into a container and at the same time diffuse the remaining liquid sterilizer in the container, the extension rod then retracts, and the liquid sterilizer remaining in the container is guided to the retracted extension rod through the valve block along with the blow air and the interior of the valve block and the extension rod are sterilized.

2. The method for sterilizing a blow molding machine according to claim 1, wherein, the remaining liquid sterilizer in the container is further guided into a chamber surrounding the blow molding machine after being guided to the retracted extension rod through the valve block along with the blow air.

3. The method for sterilizing a blow molding machine according to claim 1, wherein an interior of the molding die of the blow molding machine is also sterilized by blasting the blow air into the preform to expand and break the preform, thereby diffusing the remaining liquid sterilizer.

4. The method for sterilizing a blow molding machine according to claim 1, wherein the preform is blow-molded after the liquid sterilizer is made to adhere to an outer surface of the preform.

5. The method for sterilizing a blow molding machine according to claim 1, wherein the liquid sterilizer contains one or both of a hydrogen peroxide constituent and an ethanol constituent.

* * * * *